United States Patent
Kulkarni et al.

(10) Patent No.: US 9,199,913 B2
(45) Date of Patent: Dec. 1, 2015

(54) PROCESS FOR CONTINOUS FLOW SYNTHESIS OF BETA-AMINO CROTONATE

(75) Inventors: Arvind A. Kulkarni, Pune (IN); Anna R. Joshi, Pune (IN); Ramesh R. Joshi, Pune (IN)

(73) Assignee: Council of Scientific & Industrial Research (IN)

( * ) Notice: Subject to any disclaimer, the term of this patent is extended or adjusted under 35 U.S.C. 154(b) by 0 days.

(21) Appl. No.: 14/113,804

(22) PCT Filed: Apr. 25, 2012

(86) PCT No.: PCT/IN2012/000302
§ 371 (c)(1),
(2), (4) Date: Oct. 24, 2013

(87) PCT Pub. No.: WO2012/147103
PCT Pub. Date: Nov. 1, 2012

(65) Prior Publication Data
US 2014/0046090 A1    Feb. 13, 2014

(30) Foreign Application Priority Data

Apr. 25, 2011 (IN) ............................ 1205/DEL/2011
Mar. 2, 2012 (IN) ............................. 598/DEL/2012

(51) Int. Cl.
*C07C 229/00* (2006.01)
*C07C 227/06* (2006.01)

(52) U.S. Cl.
CPC ................................... *C07C 227/06* (2013.01)

(58) Field of Classification Search
CPC .. C07C 227/06; C07C 229/30; H04L 1/0045; H04L 1/0069; H04L 1/0072; H04W 52/244; H04W 52/322; H04W 72/082; H04W 84/045; Y02B 60/50
USPC ........................................................ 560/172
See application file for complete search history.

(56) References Cited

U.S. PATENT DOCUMENTS 4,046,803 A * 9/1977 Heckles .................... 560/172
6,423,866 B1 * 7/2002 Braun et al. ............... 560/172
2005/0106689 A1 5/2005 Braun et al.

FOREIGN PATENT DOCUMENTS

GB    2219294 A    12/1989

OTHER PUBLICATIONS

Pashkevich et al. (Reactions of Fluoroalkyl-Beta-ketoesters with Ammonia, Institute of Chemistry, 7, 1438-1442, 1986).*
Herath et al. (One-Step Continuous Flow Synthesis of Highly Substituted Pyrrole-3-Carboxylic Acid Derivatives via in Situ Hydrolysis of tert-butyl Esters, Organic Letters, vol. 12, No. 22, pp. 5182-5185, 2010).*
Brandt, Carlos A., et al.; Efficient Synthetic Method for β-Enamino Esters Using Ultrasound; pp. 1557-1559; (2004); No. 10; Synthesis.
Anderson, P.C. et al.; 2-Aryl-3-Acetyl-4(1H)-quinolones; pp. 3033-3037; (1965); vol. 30; Journal of Organic Chemistry.
Toja, E. et al.; Pyrrolidine Analogs of Nalidixic Acid, 2. Pyrrolo[3,4-b]pyridines; pp. 1561-1564; (1986); vol. 23; Journal of Heterocyclic Chemistry.
International Search Report dated Oct. 23, 2012.

* cited by examiner

*Primary Examiner* — Yevegeny Valenrod
*Assistant Examiner* — Blaine G Doletski
(74) *Attorney, Agent, or Firm* — Blank Rome LLP

(57) ABSTRACT

Beta aminocrotonates are important intermediates for the synthesis of Ca channel blockers. The processes available in the art are batch processes with yields about 85%. There are no continuous processes available for the synthesis of such compounds. This gap in the art is addressed by the invention by disclosing a continuous process resulting in high yields of beta amino crotonates.

5 Claims, 2 Drawing Sheets

PROCESS FOR CONTINOUS FLOW SYNTHESIS OF BETA-AMINO CROTONATE

This application is a U.S. national phase of International Application No. PCT/IN2012/000302, filed Apr. 25, 2012, which claims the priority of Indian Patent Application Nos. 1205/DEL/2011, filed Apr. 25, 2011 and 0598/DEL/2012, filed Mar. 2, 2012, the disclosures of which are incorporated herein by reference.

FIELD OF THE INVENTION

The invention relates to process for the synthesis of β-amino crotonate. Particularly, the invention discloses a continuous flow synthesis for the preparation of β-amino crotonates.

BACKGROUND AND PRIOR ART OF THE INVENTION

β-amino crotonate are compounds of interest since they find use as intermediates for the synthesis of Ca channel blockers such as Nisoladipine, Benidipine, Nicardipine and such type of compounds, in the preparation and purification of various metals and as a catalyst for polymerization.

Several batch synthesis processes are disclosed in patent and non patent literature or such types of compounds.

U.S. Pat. No. 4,046,803 titled "Method Of Preparing β-Amino Derivatives Of α, β-Unsaturated Esters" discloses a method for the preparation of β-amino derivatives of α, β-unsaturated esters of the formula $CH_3C(NH_2)=CHCOOR'$ where R' is $C_1$ to $C_{10}$ linear or branched alkyl or substituted $C_1$ to $C_{10}$ linear or branched alkyl. A reaction mixture of an acetoacetate ester of the formula $CH_3C(O)CH_2C(O)OR'$ wherein R' is the same as defined above is first formed in an organic solvent and this mixture reacted with aqueous ammonium hydroxide in the presence of a salt of ammonia or of a metal selected from the group consisting of lithium, zinc, cadmium, cerium and lead. The salt is soluble in the organic solvent to an extent sufficient to catalyze the reaction between ammonia and the ester. The reaction product is readily recovered simply by extracting the solution with a solvent that dissolves the δ-amino a,δ-unsaturated ester. But this process definitely requires the addition of a salt of ammonia or a metal in spite of addition of aqueous ammonium hydroxide, such that salt is soluble in the organic solvent to an extent sufficient to catalyze the reaction between ammonia and the ester.

U.S. Pat. No. 4,448,964 titled "1,4-Dihydropyridine derivatives" uses a process for preparation of 1,4-Dihydropyridine derivatives described in B. Loev, et al, J. Medicinal Chem., 17, 956 (1974) in Process No. 2 which is reproduce as follows:

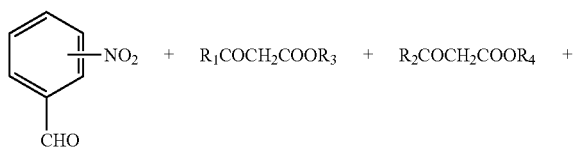

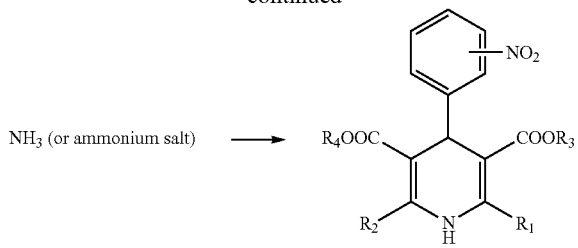

The yield in the process is between 20-50%.

But there is no prior art disclosing a continuous flow synthesis process of β-amino crotonates. Further, there are no prior arts that disclose processes that afford high yield of beta amino crotonates.

To fulfill this gap in the art, the inventors disclose a continuous flow synthesis, process for β-amino crotonates.

Further, the invention includes a solvent free catalytic process for the synthesis of β-amino crotonate resulting in pure β-amino crotonate.

SUMMARY OF THE INVENTION

Accordingly, continuous process for the synthesis of beta aminocrotonates, the process comprising reacting a ketonic ester with a base optionally in presence of an organic solvent and an acid catalyst to obtain the said beta aminocrotonates.

In an embodiment of the present invention, the ester is methyl aceto acetate or ethyl acetoacetate.

In another embodiment of the present invention, said base is selected from the group consisting of ammonia, methylamine, ethylamine and tertiary butylamine.

In yet another embodiment of the present invention, the organic solvent is an alcohol selected from the group consisting of methanol, ethanol or isopropanol.

In yet another embodiment of the present invention, ratio of said base to said ester is 1:3 to 3:1.

In yet another embodiment of the present invention, ratio of said base, ester and the solvent is 1:3:0 to 3:1:3.

In yet another embodiment of the present invention, said catalyst is an aliphatic carboxylic acid selected from acetic acid or n-propanoic acid.

In yet another embodiment of the present invention, the reaction is performed at a temperature ranging between 20-60° C.

In yet another embodiment of the present invention, the beta aminocrotonates obtained by the process yields in the range of 93% to 100%.

In yet another embodiment of the present invention, the representative beta aminocrotonates are methyl amino crotonate, ethyl amino crotonate, tertiary butyl amino crotonate, methyl 3-methyl aminocrotonate, ethyl 3-methyl aminocrotonate, methyl 3-butyl aminocrotonate and butyl 3-ethyl aminocrotonate.

In yet another embodiment of the present invention, said process is a non-cryogenic process.

In yet another embodiment of the present invention, the base used is recycled.

In yet another embodiment of the present invention, an acid is added, such as acetic acid to reduce the reaction time, and is thus used as a catalyst.

In yet another embodiment of the present invention, process is carried out in a tubular reactor, reducing reaction times but yet yielding products with comparable yields.

In yet another embodiment of the invention, with reference to FIG. 1, the process needs continuous supply of only methyl acetoacetate and ammonia to obtain zero water discharge reaction. This reaction is exemplified herein resulting in yield of greater than 90% on repeated cycles.

DETAILED DESCRIPTION OF THE INVENTION

In accordance with the objectives of the invention, the inventors disclose a continuous flow synthesis process for β-amino crotonate comprising: reacting a base with an ester in the presence of an organic solvent in ratios ranging from 1:3:0 to 3:1:3 to obtain β-amino crotonate of purity greater than 99.98% and yield greater than 93%.

Such β-amino crotonates are further reacted with benzilidines to obtain Ca channel blockers.

The esters used for the process are methyl acetoacetate, ethyl acetoacetate, and such like.

The base is selected from ammonia, methylamine, ethylamine, tertiary butylamine and such like. The base used is recycled. The process an acid is added, such as acetic acid to reduce the reaction time, and is thus used as a catalyst.

The solvent of the process is preferably isopropanol.

The drying time is programmed to result in crystals of β-amino crotonate that required no further purification.

The process is carried out in a tubular reactor, reducing reaction times but yet yielding products with comparable yields.

The continuous flow synthesis process of β-amino crotonate of the invention can be carried out in batch mode too.

Experiments were carried out by mixing methyl acetoacetate with aqueous ammonia (25% solution) at room temperature. Experiment was carried out with and without isopropanol as the solvent media. With the Methyl aceto acetate to ammonia ratio, of 1:1, 1:2 and 1:3 in identical amounts of solvent, the reaction time decreased from 180 min to 75 min with yield of the methyl amino crotonate increasing from 59% to 73%. With the Methyl aceto acetate to ammonia to solvent ratio of 1:2:0, 1:2:1, and 1:2:3, the reaction time for complete conversion of methyl aceto acetate increased from 75 min to 120 min, the yield also increased from 59% to 86%.

Experiments were also carried out by mixing methyl acetoacetate with aqueous ammonia (25% solution) at different temperatures. With an increase in the batch temperature from 25 degree C. to 50 degree C., the yield decreased from 78% to 52%.

Figure 1:
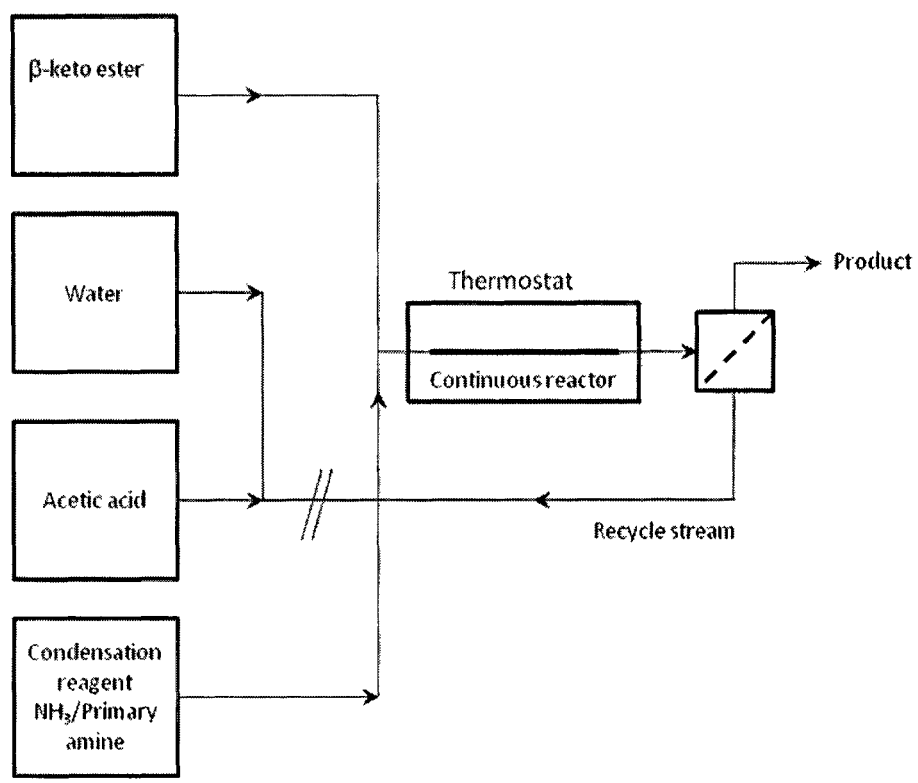
FIG. 1: Set-up for zero water discharge continuous process for synthesis of β-amino crotonate requiring continuous supply of only methyl acetoacetate and ammonia.

With reference to FIG. 1, the process needs continuous supply of only methyl acetoacetate and ammonia to obtain zero water discharge reaction. This reaction is exemplified herein resulting in yield of greater than 90% on repeated cycles.

The continuous process of the invention is carried out at temperature ranging from room temperature to 50° C., unlike prior art processes that are generally carryout out at cryogenic temperatures to avoid loss of ammonia and to contain exothermic nature of the reaction.

EXAMPLES

Following examples are given by way of illustration therefore should not be construed to limit the scope of the invention.

Example 1

Process for the Preparation of Methyl Amino Crotonate

Continuous flow experiment was carried out in a SS316 tubular reactor of 6.35 mm o.d. and 2 m length at 50° C. with a residence time of 15 min. The Methyl aceto acetate to ammonia to solvent iso-propanol ratio was 1:3:1, and the yield of methyl amino crotonate was 56%.

Example 2

Process for the Preparation of Methyl Amino Crotonate

Continuous flow experiment was carried out in a SS316 tubular reactor of 6.35 mm o.d. and 2 m length at 50° C. in presence of ultrasonic field with a residence time of 15 min. The Methyl aceto acetate to ammonia to solvent ratio was 1:3:0, and the yield of methyl amino crotonate was 54%. No choking of reactor was observed.

Example 3

Process for the Preparation of Methyl Amino Crotonate

Continuous flow experiment was carried out in a SS316 tubular reactor of 6.35 mm o.d. and 2 m length at 50 C with a residence time of 15 min in the absence of any solvent and without sonication. The Methyl aceto acetate to ammonia ratio of 1:3 resulted in the yield of methyl amino crotonate of 48%. No choking of reactor was observed.

Example 4

Process for the Preparation of Methyl Amino Crotonate

Continuous flow experiment was carried out in a SS316 tubular reactor of 6.35 mm o.d. and 2 m length at 50° C. with a residence time of 15 min in the absence of any solvent and without sonication. The Methyl aceto acetate to ammonia ratio of 1:2, the yield of methyl amino crotonate observed was 59%. No choking of reactor was observed.

Example 5

Process for the Preparation of Methyl Amino Crotonate

Continuous flow experiment was carried out in a SS316 tubular reactor of 6.35 mm o.d. and 2 m length at 50° C. with a residence time of 120-160 s without any solvent. The Methyl aceto acetate to ammonia to catalyst (Acetic acid)— volume ratio of 1:3:0.5 yielded 94% methyl amino crotonate from the first crop. No choking of reactor was observed.

Example 6

Process for the Preparation of Methyl Amino Crotonate

Continuous flow experiment was carried out in a SS316 tubular reactor of 6.35 mm o.d. and 3 m length at 50° C. with a residence time of 120-160 s without any solvent with the inlet composition as in Example 7. The hourly yield of the product methyl amino crotonate was 700 gm. ie. 93% yield.

Example 7

Process for the Preparation of Ethyl Amino Crotonate

Continuous flow experiment was carried out in a SS316 tubular reactor of 1.58 mm o.d. by mixing ethyl acetoacetate with aqueous ammonia (25% solution) using a simple T-mixer and reactor with 1 m length having a residence time of 22 min. Product yields was 73% at 20° C.

Example 8

Process for the Preparation of Ethyl Amino Crotonate

Continuous flow experiment was carried out in a SS316 tubular reactor of 1.58 mm o.d. by mixing ethyl acetoacetate with aqueous ammonia (25% solution) in the ration 1:3 using a simple T-mixer and reactor with 1 m length having a residence time of 22 min. Product yields was 84% at 30° C.

Example 9

Process for the Preparation of Ethyl Amino Crotonate

Continuous flow experiment was carried out in a SS316 tubular reactor of 1.58 mm o.d. by mixing ethyl acetoacetate with aqueous ammonia (25% solution) in the ratio 1:3 using a simple T-mixer and reactor with 1 m length having a residence time of 22 min. Product yields was 94% at 50° C.

Example 10

Process for the Preparation of Methyl 3-methyl Amino Crotonate

Continuous flow experiment was carried out in a SS316 tubular reactor of 1.58 mm o.d. by mixing methyl acetoacetate with methyl amine in isoproponol in the ratio 1:3 using a simple T-mixer and reactor with 1 m length at 40 C. Complete conversion of the substrates is observed in 30 s. ie 100% yield.

Example 11

With reference to FIG. 1, set-up for reaction which needs continuous supply of only methyl acetoacetate and ammonia to obtain zero water discharge reaction is exemplified.

Figure 2:
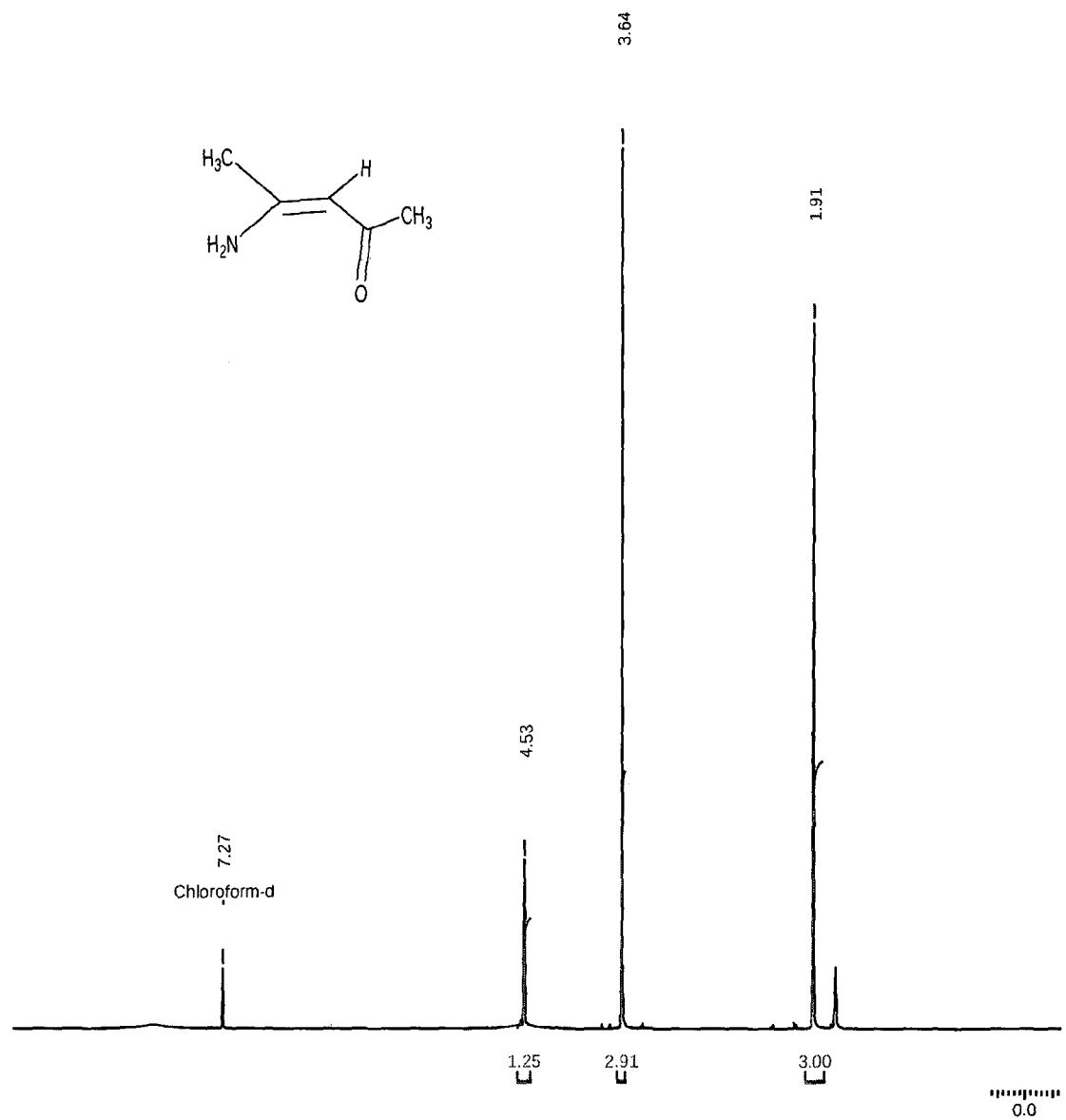
FIG. 2: $^1$H NMR of methyl amino crotonate.

Methyl acetoacetate (1 mol)=116 gm (Expected yield of the product for 100% conversion =115 gm) when reacted with Aq. Ammonia (2 mol) (MAA:NH3:1:2) and Acetic acid (1 mol) as a catalyst at 50° C. in a tubular reactor for 160 s, it yielded 95.9 gm methyl amino crotonate (86% yield). Filtrate was saturated with gaseous ammonia and was resent to the reactor through a T-mixer with another stream containing only the methyl acetoacetate. Reaction was carried out for reacting 1 mol of the reactant with the ammonia saturated filtrate for all other conditions as mentioned above. The product yield was 101.1 gm (87.8% yield). Upon repeating the filtration, saturation, recycle and reuse of the solution containing acetic acid for the third time and reacted with 1 mol of methyl acetoacetate it yielded 105.8 gm (92% yield) of product. The process thus becomes a zero water discharge process and eventually it achieves a steady state yield of 98%. The maximum loss of acetic acid per recycle was less than 2%. Methyl amino crotonate synthesized by the examples provided herein was characterized by NMR as shown in FIG. 2. $^1$H NMR (400 MHz, CDCl3) showed δ 4.53 (s, 1H,C=C$\underline{H}$), 3.64 (s, 3H, C$\underline{H_3}$C=O), 1.91 (s, 3H, C$\underline{H_3}$). The compound was also characterized by mp and found to be 81.9-82.5 (lit 81-83)

Advantages of the Invention

1. Continuous process with high yields.
2. Non cryogenic process.
3. Organic solvent process.
4. Zero discharge process with base and catalyst recycled.

We claim:

1. A continuous process for the synthesis of beta aminocrotonates, the process comprising reacting an ester of acetoacetate with a base selected from the group consisting of ammonia, methylamine, ethylamine and tertiary butylamine, optionally in the presence of an acid catalyst to obtain the said beta aminocrotonates, wherein the process is accomplished without the use of a solvent and is performed at a temperature ranging between 20-60° C., and the beta aminocrotonates are obtained in greater than 93% yield.

2. The process of claim 1, wherein the ester is methyl acetoacetate or ethyl acetoacetate.

3. The process of claim 1, wherein ratio of said base to said ester is 1:3 to 3:1.

4. The process of claim 1, wherein said catalyst is an aliphatic carboxylic acid selected from acetic acid or n-propanoic acid.

5. The process of claim 1, wherein the beta aminocrotonates is methyl amino crotonate, ethyl amino crotonate, or tertiary butyl amino crotonate.

* * * * *